United States Patent
Hansenne et al.

(10) Patent No.: US 10,470,988 B2
(45) Date of Patent: Nov. 12, 2019

(54) SKIN IMPROVEMENT FORMULATIONS

(71) Applicant: Coty Inc., New York, NY (US)

(72) Inventors: Isabelle Hansenne, Westfield, NJ (US); Muriel Pujos, West New York, NJ (US); Katherine Lee, New City, NY (US)

(73) Assignee: Coty Inc., New York, NY (US)

(*) Notice: Subject to any disclaimer, the term of this patent is extended or adjusted under 35 U.S.C. 154(b) by 0 days.

(21) Appl. No.: 15/747,689

(22) PCT Filed: Jul. 27, 2016

(86) PCT No.: PCT/US2016/044308
§ 371 (c)(1),
(2) Date: Jan. 25, 2018

(87) PCT Pub. No.: WO2017/019793
PCT Pub. Date: Feb. 2, 2017

(65) Prior Publication Data
US 2018/0221258 A1    Aug. 9, 2018

Related U.S. Application Data

(60) Provisional application No. 62/197,307, filed on Jul. 27, 2015.

(51) Int. Cl.
*A61Q 19/02* (2006.01)
*A61K 8/365* (2006.01)
(Continued)

(52) U.S. Cl.
CPC .......... *A61K 8/365* (2013.01); *A61K 8/0208* (2013.01); *A61K 8/345* (2013.01); *A61K 8/362* (2013.01);
(Continued)

(58) Field of Classification Search
CPC .......... A61K 2800/87; A61K 2800/88; A61K 8/0208; A61K 8/345; A61K 8/362;
(Continued)

(56) References Cited

U.S. PATENT DOCUMENTS 6,346,255 B1 * 2/2002 Fotinos .............. A61K 8/0208
424/401
2009/0068255 A1    3/2009 Yu et al.
(Continued)

FOREIGN PATENT DOCUMENTS

CN        103462845 A    12/2013
WO    WO-2006/106992 A1    10/2006
(Continued)

OTHER PUBLICATIONS

The Seaweed Site [online] retrieved on Dec. 26, 2018 from: http://www.seaweed.ie/descriptions/Halidrys_siliquosa.php; 2 pages. (Year: 2018).*
(Continued)

*Primary Examiner* — Ernst V Arnold
(74) *Attorney, Agent, or Firm* — Schwegman Lundberg & Woessner, P.A.

(57) ABSTRACT

Inventive embodiments disclosed herein include formulation embodiments for promoting a reduction in skin pigmentation. The inventive formulation embodiments Hibiscus acids, a Halidrys formulation that includes water; glycerin; Sargassum Muticum Extract and one or more alpha hydroxyl acids in concentrations for reducing melanin concentrations in melanin containing cells upon contact.

11 Claims, 7 Drawing Sheets

(51) Int. Cl.
*A61K 8/362* (2006.01)
*A61K 8/97* (2017.01)
*A61K 8/34* (2006.01)
*A61K 8/02* (2006.01)
*A61K 8/96* (2006.01)

(52) U.S. Cl.
CPC .................. *A61K 8/96* (2013.01); *A61K 8/97* (2013.01); *A61Q 19/02* (2013.01); *A61K 2800/87* (2013.01); *A61K 2800/88* (2013.01)

(58) Field of Classification Search
CPC . A61K 8/365; A61K 8/96; A61K 8/97; A61Q 19/02
See application file for complete search history.

(56) References Cited

U.S. PATENT DOCUMENTS

| 2011/0229538 | A1 | 9/2011 | Matravers et al. | |
|---|---|---|---|---|
| 2015/0250709 | A1* | 9/2015 | Gan | A61K 8/8141 424/62 |
| 2016/0000696 | A1* | 1/2016 | Mei | A61Q 19/00 424/62 |

FOREIGN PATENT DOCUMENTS

| WO | WO-2014/158854 A1 | 10/2014 |
|---|---|---|
| WO | WO-2017/019793 A1 | 2/2017 |

OTHER PUBLICATIONS

Definition of "include" [online] retrieved on Dec. 27, 2018 from: https://en.oxforddictionaries.com/definition/us/exacerbate; 4 pages. (Year: 2018).*

Hansawasdi et al. (Biosci.Biotechnol. Biochem. 2001;65(9):2087-2089). (Year: 2001).*

"International Application Serial No. PCT/US2016/044308, International Preliminary Report on Patentability dated Feb. 8, 2018", 10 pgs.

"International Application Serial No. PCT/US2016/044308, International Search Report dated Oct. 20, 2016", 3 pgs.

"International Application Serial No. PCT/US2016/044308, Written Opinion dated Oct. 20, 2016", 8 pgs.

* cited by examiner

SKIN IMPROVEMENT FORMULATIONS

CLAIM OF PRIORITY

This patent application is a U.S. National Stage Filing under 35 U.S.C. 371 of International Patent Application Serial No, PCT/US2016/044308, filed on Jul. 27, 2016 and published as WO 2017/019793 A1, on Feb. 2, 2017, which application claims the benefit of priority to U.S. Provisional Patent Application Ser. No. 62/197,307, filed on Jul. 27, 2015, which applications and publication are hereby incorporated by reference herein in their entirety.

FIELD

Inventive embodiments disclosed herein are directed to formulation embodiments for promoting a reduction in skin pigmentation.

BACKGROUND

Hyperpigmentation is characterized by an excess production of melanin. One type of hyperpigmentation is local and is viewable as brown spots on the face and back of the hand of people impacted. Hyperpigmentation is caused by excessive exposure to the sun, damage, such as is caused by acne vulgaris, and age. Historically, hyperpigmentation has been treated with hydroquinone, kojic acid, alpha hydroxy acids, azelaic acid, ascorbic acid, tretinoin, topical glucocorticoids, and licorice extract.

SUMMARY

Inventive embodiments disclosed herein include formulation embodiments for promoting a reduction in skin pigmentation. The inventive formulation embodiments include Hibiscus acids, a Halidrys formulation that includes water, glycerin and Sargassum Muticum Extract and one or more alpha hydroxyl acids in concentrations effective for reducing melanin concentrations in melanin containing cells, upon contact.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document arc incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Inventive embodiments disclosed herein include a formula for promoting a reduction in skin pigmentation. The formula is a triple acid pad peel. The formulation includes Hibiscus acids, a Halidrys formulation that, for one embodiment, includes water in a concentration of 48.1%; glycerin in a concentration of 50.000%; and Sargassum Muticum Extract in a concentration of 1.9000% and one or more alpha hydroxyl acids in concentrations effective for reducing melanin concentrations in melanin containing cells upon contact.

One formula embodiment includes three phases. Phase A includes the following:

| Phase A | |
|---|---|
| Ingredient | Wt. Percent |
| Deionized Water | 21.75-80.00 |
| Malic Acid | 0.100-5.00 |
| Niacinamide | 0.0500-5.00 |
| Hibiscus Acids | 0.100-2.00 |
| Formulation of Glycolic Acid | 0.500-10.000 |
| Adenosine | 0.100-1.00 |
| Glycereth-7 triacetate | 5.00-10.00 |
| Polyolprepolymer-15 | 0.100-1.00 |

Concentration ranges disclosed refer to the weight percent concentrations of the overall formula of Phase A, Phase B and Phase C. The Hibiscus acids component of Phase A includes a formulation that includes, for one embodiment, 92.4990% Hibiscus Sabdariffa Flower Extract; 7.5000% magnesium hydroxide; and 0.0010% of sulfates of the Hibiscus Acids formulation.

The formulation of the Glycolic Acid ingredient of Phase A includes glycolic acid in a concentration of 64.000% of the glycolic acid formulation; water in a concentration of 26.000%; and arginine in a concentration of 10% by weight of the formulation of glycolic acid.

The polyolprepolymer-15 ingredient of Phase A includes PEG-8/SMDI copolymer in a concentration of 99.9700 of the polyolprepolymer-15 formulation and 0.0300% of isocyanate.

| Phase B: | |
|---|---|
| Ingredient | Wt. Percent |
| Dragosantol 100 | 0.100-1.00 |

The Dragosantol 100 formulation of Phase B includes 98.4% Bisabolol; 1% Farnesol; 0.5000% alcohol; 0.5000 acetone; 10.000% water; 35.000% PEG-40 hydrogenated castor oil; and 55.000% PPG-26-Buteth-26 of the Dragosantol 100 formulation. The Bisabolol is a synthetic racemic mixture of D and L forms of Bisabolol.

| Phase C: | |
|---|---|
| Ingredient | Wt. % |
| Sodium Hydroxide Pellets | 0.100-1.00 |
| Concentre Halidrys G | 0.100-4.00 |
| Alcohol | 15.000-35.00 |
| DL-Mandelic Acid | 0.500-5.00 |

The Concentre Halidrys G includes water in a concentration of 48.1%; glycerin in a concentration of 50.000%; and Sargassum Muticum Extract in a concentration of 1.9000% of the Concentre Halidrys G formulation. The Sargassum muticum algae aids in decreasing melanin synthesis and in limiting melanin distribution in the skin.

The alcohol formulation includes denatured alcohol in a concentration of 99.9890%; water in a concentration of 0.0100%; and acetaldehyde in a concentration of 0.0010% by weight of the alcohol formulation.

The glycolic acid, mandelic acid and malic acid act by decreasing cohesion of corneocytes and aiding their progressive elimination and by stimulating the epidermis. The three acids alter corneocyte membrane, imparting to it a sawtooth contour, inducing rupture of lipidic envelope and targeting corneodesmosomes and desmosomes. The term, "corneocytes" as used herein refers to terminally differentiated keratinocytes that make up most of the stratum corneum. The term "corneodesmosomes" as used herein refers to any of a class of proteins that hold corneocytes together. The term, "desmosomes" as used herein refers to a structure by which two adjacent cells are attached, formed from protein plaques in the cell membranes linked by filaments.

The nicotinamide or Vitamin B3 sooths skin by limiting melanin transfer from melanocytes to keratinocytes which aids in regulating melanin distribution in the skin. The soothing action aids in counteracting post inflammatory hyperpigmentation by down regulating the production of inflammatory cytokines that contribute to the over pigmentation.

The hibiscus extract includes polyphenols as well as natural organic acids such as hydroxycitric acid and hibiscus acid. The hibiscus extract is used to eliminate excess melanin in order to even skin color.

The formulation is enclosed within a container. Some embodiments additionally include an absorbent pad for transferring the formulation from the container to skin of a user. For other embodiments, the formulation impregnates at least a portion of an absorbent pad. For other embodiments, the formulation is applied to skin without a pad.

Figure 1:
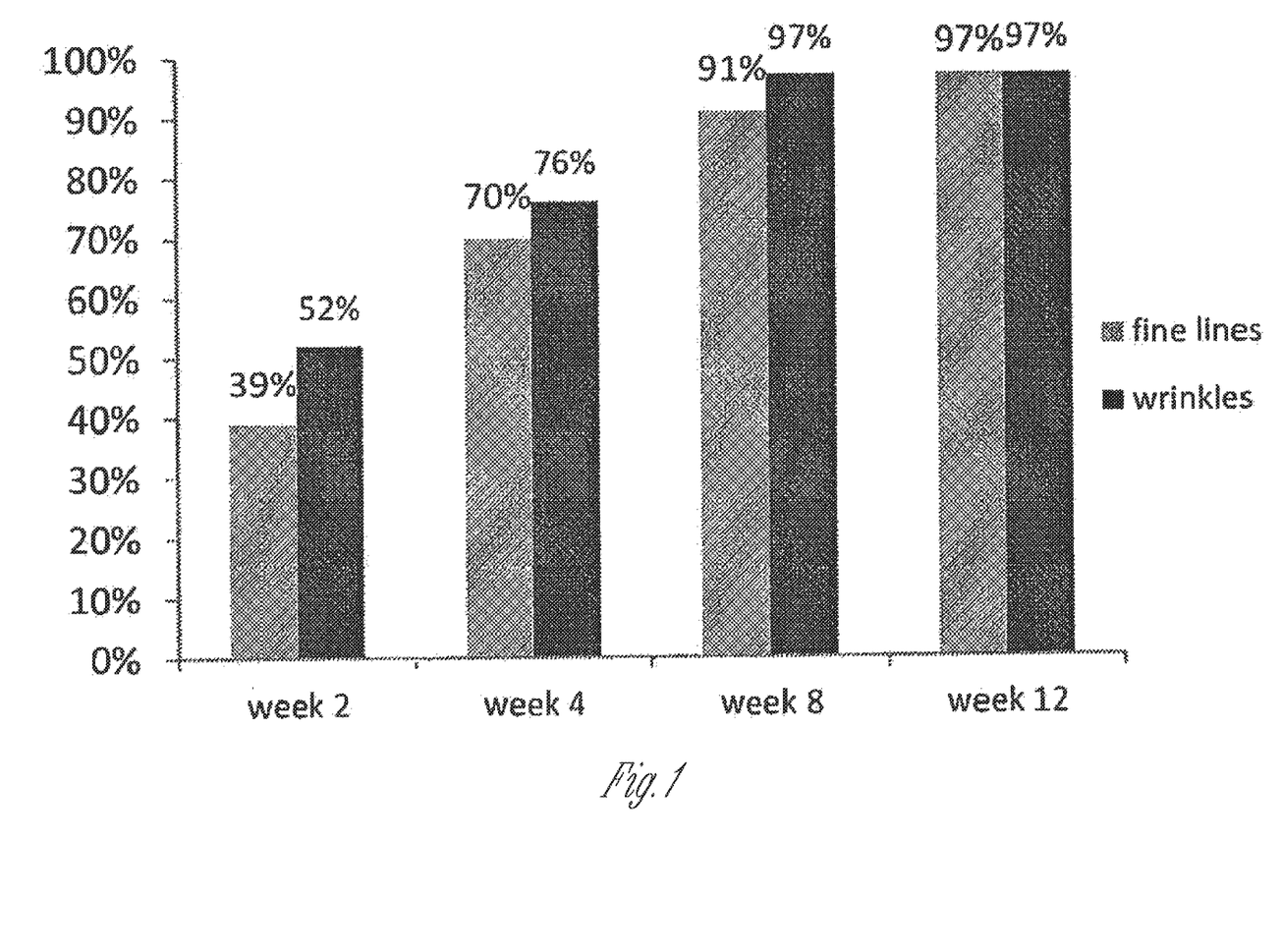
FIG. 1 is a graphical view of a percent of female test subjects showing improvement in facial fine lines and wrinkles after using an acid peel formulation embodiment disclosed herein, over twelve weeks.

A test conducted with female subjects was performed to ascertain product efficacy, as measured by improvement of fine lines and wrinkles, changes in hyperpigmentation and changes in pore size of facial skin pores. Female subjects presented with skin displaying hyperpigmentation, rough texture, fine lines, wrinkles and dilated pores. The test included weekly recording of observations of facial skin of female test subjects. Female test subjects used a formulation embodiment disclosed herein for twelve weeks, applying it once per week over their clean, dry faces. Subjects followed application with a formulation disclosed herein with their regular moisturizer. Each morning, subjects used their daily facial sunscreen. Results are shown in FIG. 1. A majority of the female subjects started showing improvement with respect to wrinkles from week 2 and best results are seen at week 8 and 12.

Figure 2:
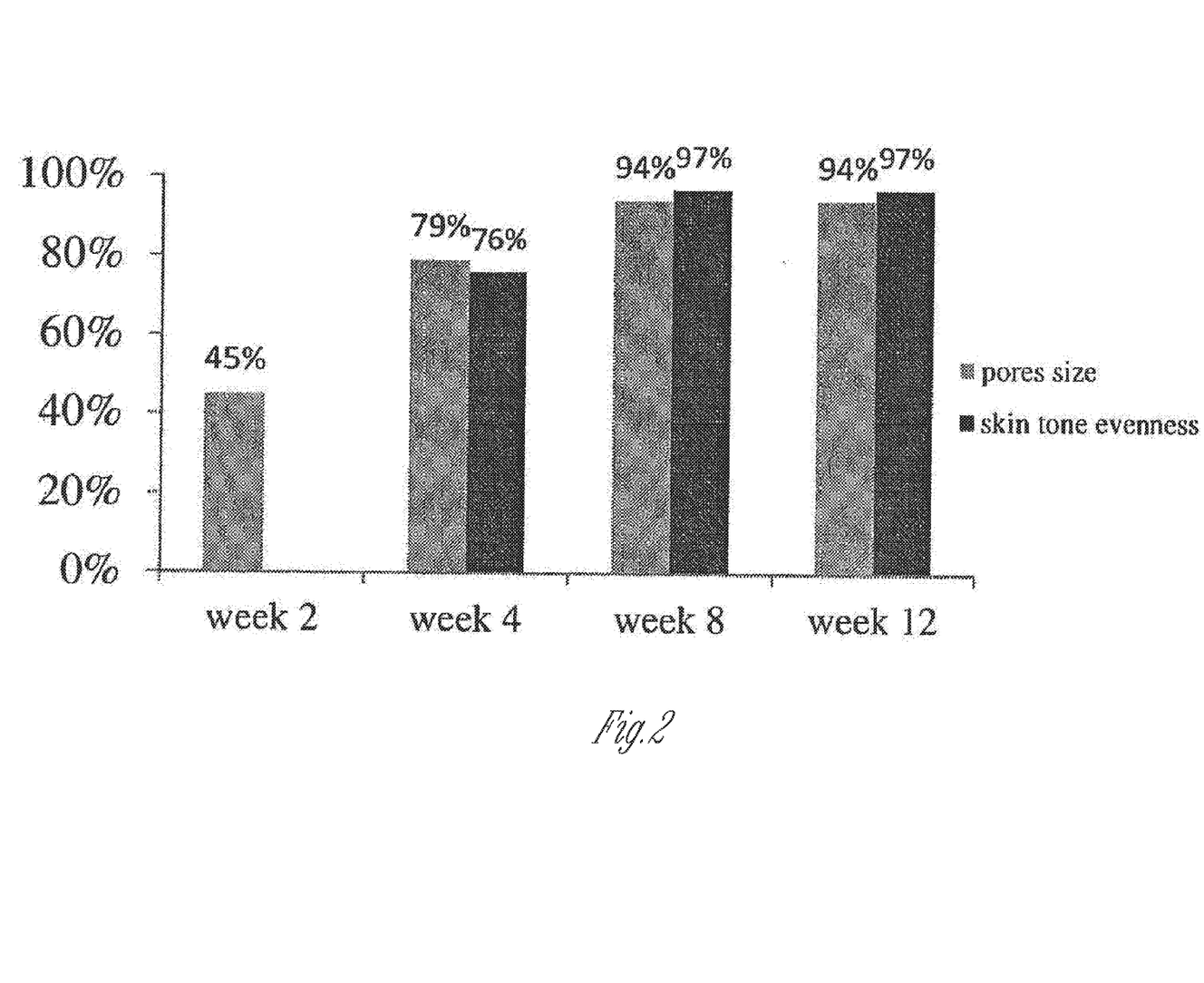
FIG. 2 is a graphical view of a percent of female test subjects showing improvement in facial skin pore size after using an acid peel formulation embodiment disclosed herein, over twelve weeks.
Figure 3:
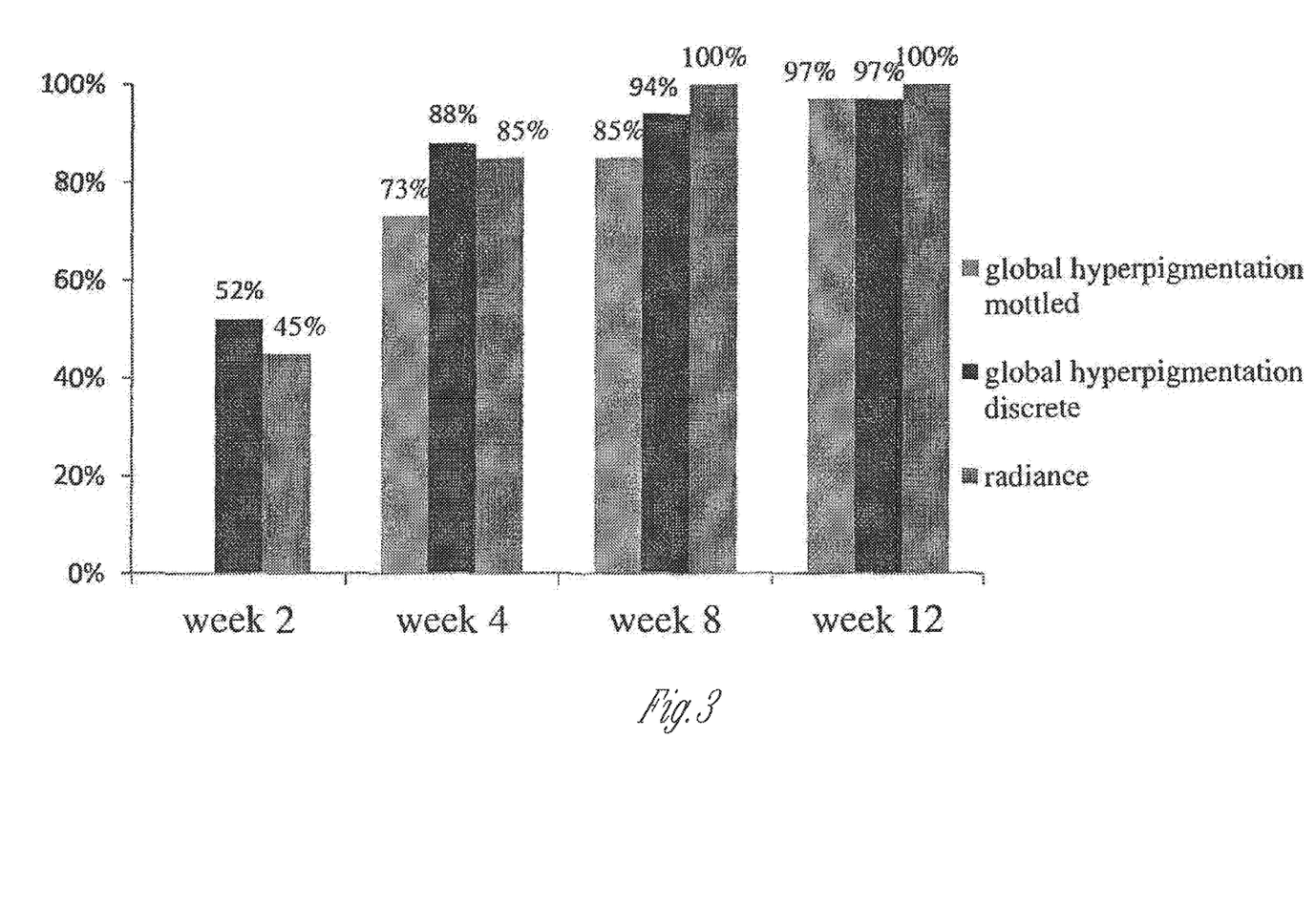
FIG. 3 is a graphical view of a percent of female test subjects showing improvement in global hyperpigmentation and radiance in facial skin after using an acid peel formulation embodiment disclosed herein, over twelve weeks.

Results also showed a significant improvement of pore size that was statistically significant from 2 weeks of treatment. Percentages of female subjects displaying pore size reduction and skin tone evenness over time is shown in FIG. 2. A majority of women started showing improvement in pore size and skin tone evenness from week 4 and best results were seen at week 8 and 12.

Results also showed a significant improvement of skin radiance that was statistically significant from 2 weeks of treatment. Results showed improvement of discrete and mottled skin hyperpigmentation that was statistically significant from 2 and 4 weeks respectively using the formulation once per week. A majority of women started showing improvement in hyperpigmentation and radiance from week 4 and best results were seen at weeks 8 and 12.

Figure 4:
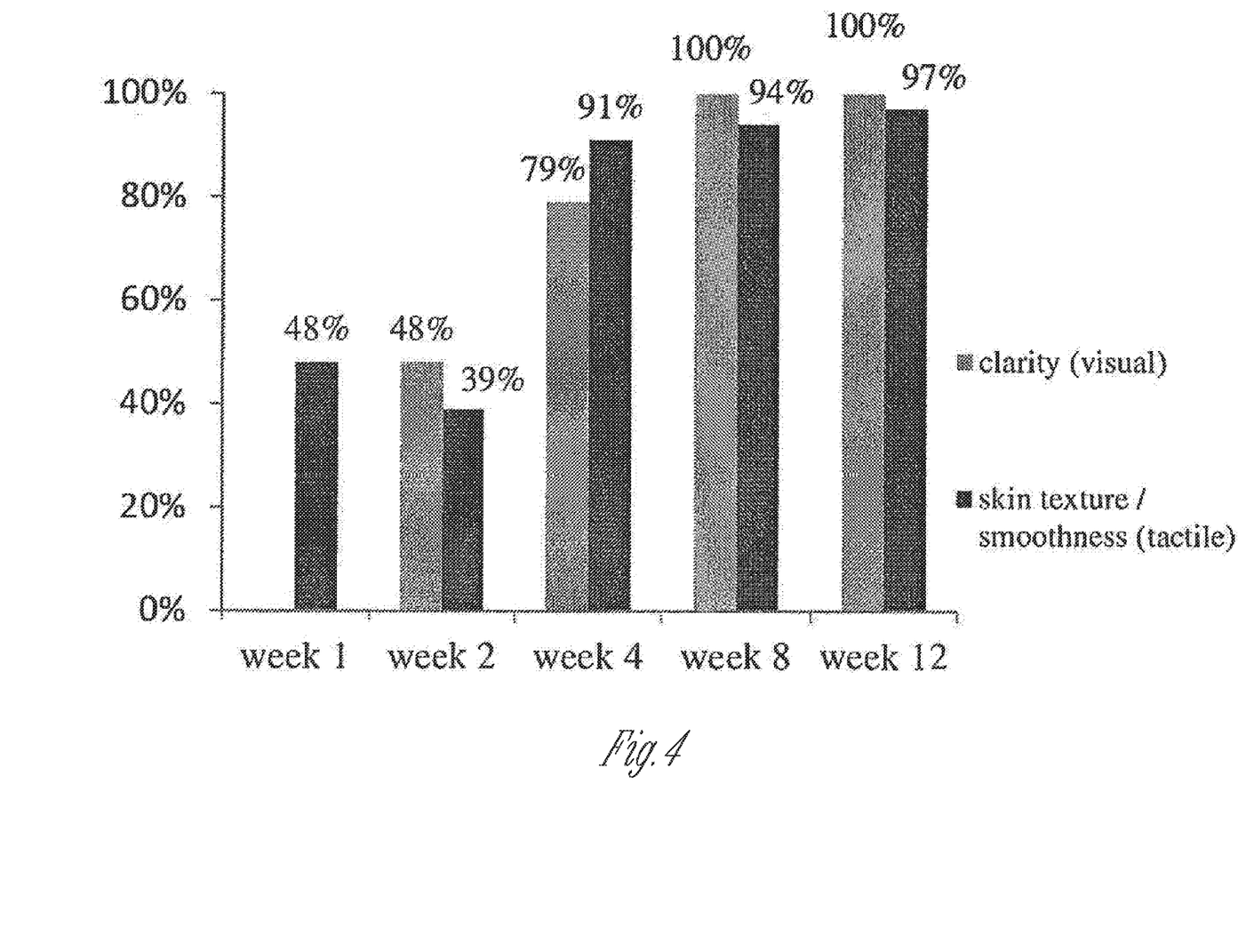
FIG. 4 is a graphical view of a percent of female test subjects showing improvement in facial skin clarity and skin texture and tactile smoothness after using an acid peel formulation embodiment disclosed herein, over twelve weeks.

Results showed a significant improvement of clarity statistically significant from 2 weeks of treatment and of skin smoothness statistically significant from week 1 using the product once per week. A majority of female subjects showed improvement in skin clarity and smoothness from week 4 and best results at weeks 8 and 12, as shown in FIG. 4.

Figure 5:
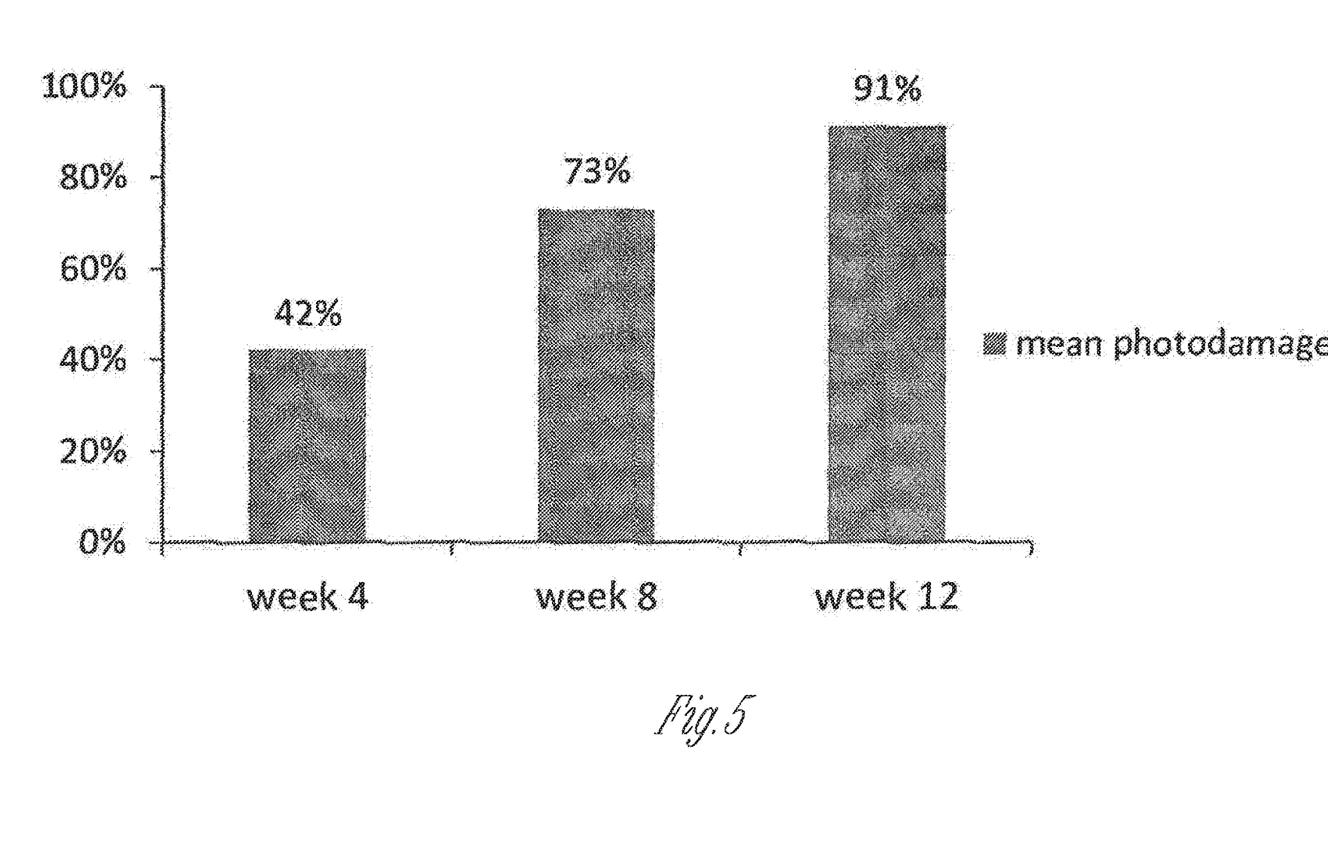
FIG. 5 is a graphical view of a percent of female test subjects showing improvement in photo damage to facial skin after using an acid peel formulation embodiment disclosed herein, over twelve weeks.

Results showed a significant improvement of mean photo damage statistically significant from 4 weeks using the formulation once per week. A majority of women started showing improvement from photo damage from week 8 and best results were seen at week 12, as shown in FIG. 5.

Under the conditions of the study disclosed herein, the formulation disposed on acid peel pads imparted an improvement in the appearance and texture of skin, compared to the appearance and texture of facial skin presented by the test subjects prior to commencement of the test.

Statistically significant improvements in fine lines, wrinkles, pore size, skin tone and evenness, mottled and discrete global hyperpigmentation, skin radiance, clarity, and skin texture and smoothness were observed following 4, 8, and 12 weeks of once a week application of acid peel pad embodiments disclosed herein. Additionally, fine lines, wrinkles, pore size, discrete global hyperpigmentation, skin radiance, clarity and skin texture and smoothness showed significant improvement following 2 weeks of test material use. Skin texture and smoothness also showed statistical improvement after 1 week of use.

Changes in facial skin color included statistically significant improvement in skin lightening at 8 and 12 weeks and statistically significant decreases in luminescence at 1, 4 and 12 weeks of test material use. Additionally, statistically significant improvements in the appearance of photo damaged skin were observed following 4, 8 and 12 weeks of once a week application of the acid peel pad embodiment.

Figure 6:
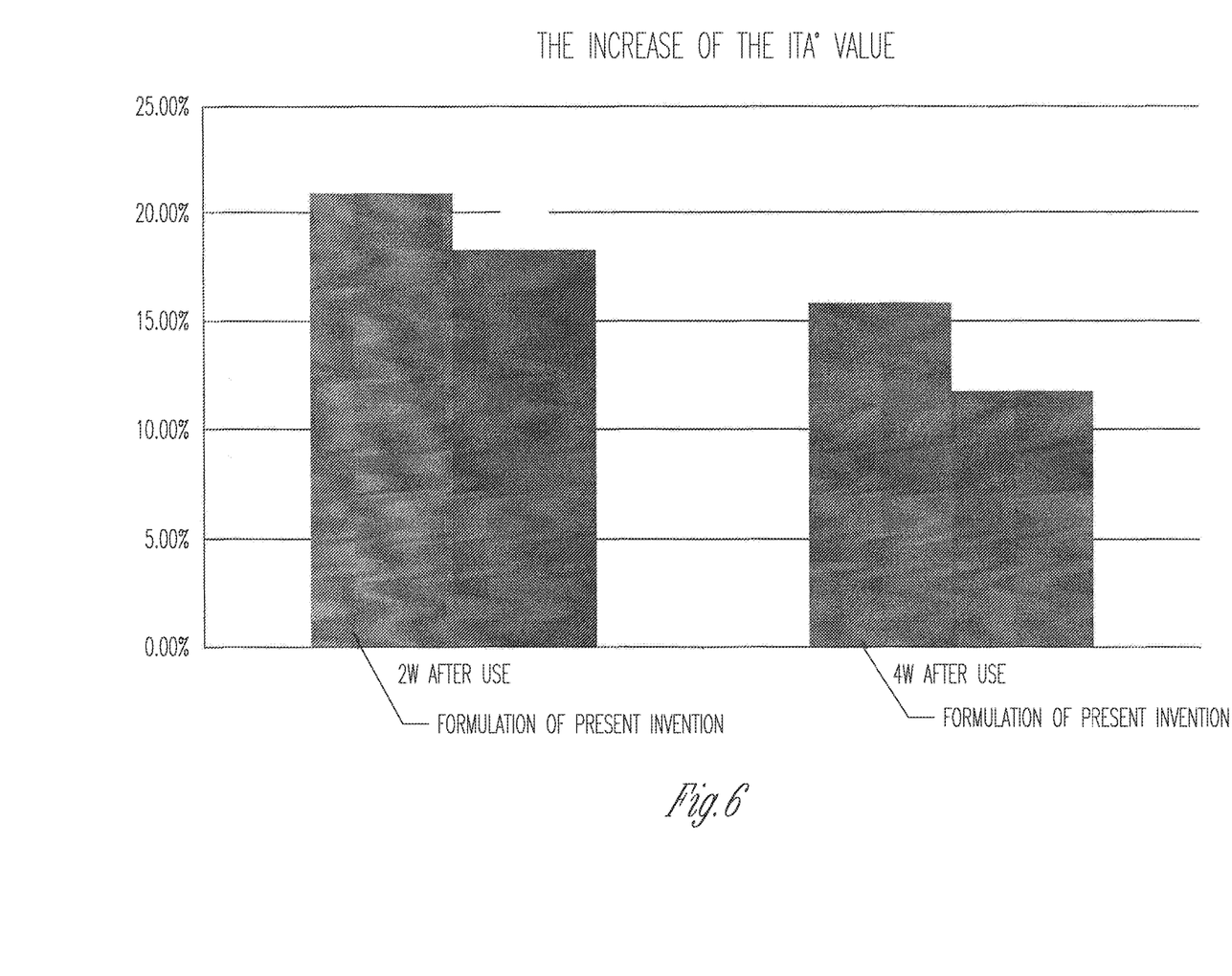
FIG. 6 is a graphical view of an increase in individual typological angle for testers using a formulation embodiment of the present invention and testers using a conventional whitening formulation.

Measurements of individual typological angle, ITA, were also performed on skin of the female subjects testing the acid peel formulation embodiment disclosed herein. The ITA index measures skin color, the higher the ITA, the fairer the skin. Another test group received a formulation with only whitening agents, not the acid peel formulations described herein. Results, displayed graphically in FIG. 6, showed a greater increase in ITA for test subjects using the acid peel formulation compared to test subjects using a formulation with only whitening agents.

Figure 7:
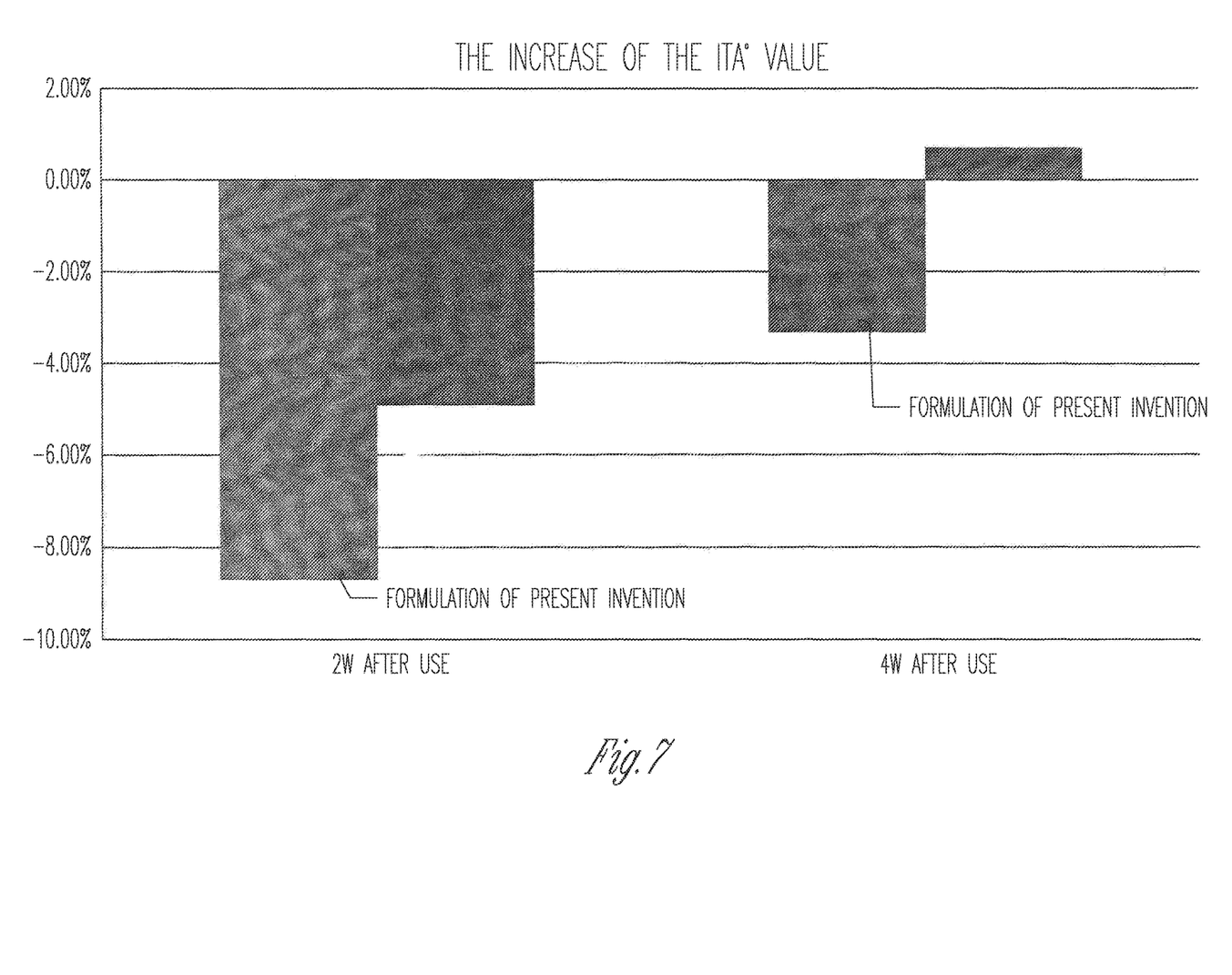
FIG. 7 is a graphical view of a change in melanin concentration in the facial skin of female test subjects using an acid peel formulation embodiment, disclosed herein, and female test subjects using a formulation having only alpha hydroxy acids.

Another study tested melanin concentration changes over time for female test subjects using acid peel formulation embodiments disclosed herein and other female test subjects using a formulation having only alpha hydroxyl acids. Results in shown in FIG. 7. The results show a greater decrease in melanin concentration in the skin of testers using the triple peel formulation embodiment compared to the skin of testers using a formulation having only alpha hydroxy acids. The greatest difference in melanin concentration changes occurred two weeks after commencement of the test. Change in melanin concentration for testers using a formulation embodiment of the present invention is shown by the light grey bar in FIG. 7. Change in melanin concentration for testers using a formulation of alpha hydroxyl acids only as an active ingredient is shown by the dark grey bar in FIG. 7.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed is:

1. A formulation for promoting a reduction in skin pigmentation, comprising: Hibiscus acids, water, glycerin, PEG-40 hydrogenated castor oil, Sargassum Muticum Extract and one or more alpha hydroxyl acids in concentrations effective for reducing melanin concentrations in melanin containing cells upon contact.

2. The formulation of claim 1, wherein the alpha hydroxyl acids comprise one or more of malic acid, glycolic acid, and mandelic acid.

3. The formulation of claim 1, further comprising a nucleic acid.

4. The formulation of claim 1, further comprising Niacinamide.

5. The formulation of claim 1, further comprising glycereth-7 triacetate.

6. The formulation of claim 1, further comprising bisabolol.

7. The formulation of claim 1, further comprising denatured alcohol.

8. A kit comprising the formulation of claim 1 and an absorbent pad.

9. The formulation of claim 1 and an absorbent pad, wherein the formulation is absorbed onto the pad.

10. A system, comprising:
    A formulation for promoting a reduction in skin pigmentation, comprising: Hibiscus acids, water, glycerin, PEG-40 hydrogenated castor oil, Sargassum Muticum Extract and one or more alpha hydroxyl acids in concentrations effective for reducing melanin concentrations in melanin containing cells upon contact; and a pad into which the formulation is absorbed.

11. The system of claim 10, further comprising a container for containing the pad and formulation.

* * * * *